United States Patent [19]

Chess et al.

[11] Patent Number: 5,773,634

[45] Date of Patent: Jun. 30, 1998

US005773634A

[54] TERTIARY BUTYL ALCOHOL ABSORPTION PROCESS FOR RECOVERING PROPYLENE AND ISOBUTANE

[75] Inventors: David Durham Chess, Houston; David George Pottratz, Beaumont; Eileen Tovan Nguyen, Houston; William Kemp Culbreth, III, Beaumont, all of Tex.

[73] Assignee: Huntsman Specialty Chemicals Corporation, Austin, Tex.

[21] Appl. No.: 749,190

[22] Filed: Nov. 14, 1996

[51] Int. Cl.[6] .......................... C07D 301/19; C07C 27/10
[52] U.S. Cl. .......................... 549/529; 568/910; 568/917
[58] Field of Search .................................. 568/910, 917; 549/529

[56] References Cited

U.S. PATENT DOCUMENTS

| | | | |
|---|---|---|---|
| 2,845,466 | 7/1958 | Pecherer | 585/320 |
| 3,351,635 | 11/1967 | Wallington | 549/529 |
| 4,296,262 | 10/1981 | Grane et al. | 568/910 |
| 4,900,850 | 2/1990 | Sanderson et al. | 549/529 |
| 4,992,602 | 2/1991 | Sanderson et al. | 568/909.8 |
| 5,414,145 | 5/1995 | Sheu et al. | 568/671 |
| 5,436,375 | 7/1995 | Thomas et al. | 568/571 |
| 5,436,376 | 7/1995 | Sheu et al. | 568/910 |
| 5,574,196 | 11/1996 | Tucker et al. | 568/838 |

*Primary Examiner*—C. Warren Ivy
*Assistant Examiner*—Lyman H. Smith
*Attorney, Agent, or Firm*—Russell R. Stolle; Carl G. Ries

[57] ABSTRACT

The liquid and gaseous products formed by reacting oxygen with isobutane in an oxidation reactor are separately processed; the liquid reaction product being charged to a distillation zone and separated into a lower boiling isobutane fraction and a higher boiling fraction comprising tertiary butyl alcohol and tertiary butyl hydroperoxide; the gaseous reaction product comprising inert gases and vaporized and/or entrained isobutane being cooled by an amount sufficient to condense isobutane contained therein for recycle to the oxidation reactor; the remaining gases, including isobutane being charged to a tertiary butyl alcohol absorber to obtain a solution of isobutane in tertiary butyl alcohol that is recycled to the distillation zone.

3 Claims, 1 Drawing Sheet

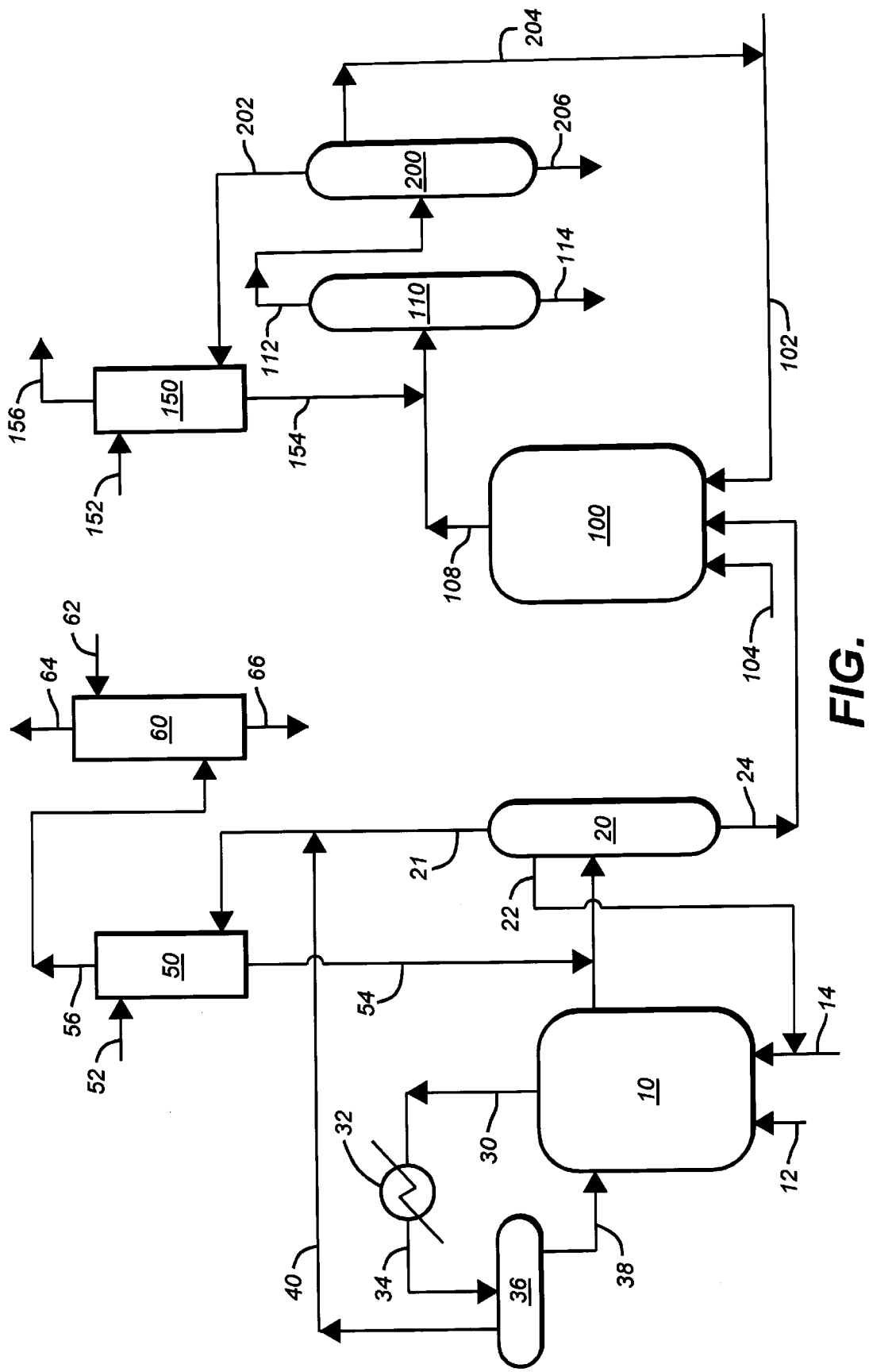

TERTIARY BUTYL ALCOHOL ABSORPTION PROCESS FOR RECOVERING PROPYLENE AND ISOBUTANE

BACKGROUND OF THE INVENTION

1. Technical Field of the Invention

This invention relates to a process for recovering vaporized hydrocarbons such as propylene and isobutane from gaseous products removed from a reactor. More particularly, this invention relates to a tertiary butyl alcohol absorption process for recovering vaporized hydrocarbons such as propylene and isobutane from inert, non-condensable gaseous products removed from a reactor. Still more particularly, this invention relates to a method for the manufacture and recovery of tertiary butyl alcohol by the oxidation of isobutane and to the manufacture of propylene oxide by the epoxidation of propylene with tertiary butyl hydroperoxide wherein propylene and isobutane are recovered by absorption from their gaseous products.

2. Prior Art

Winkler et al. U.S. Pat. No. 2,845,461 discloses a process for the non-catalytic reaction of isobutane with oxygen under reaction conditions including a temperature of about 100° to about 150° C., a pressure of about 400 to 1000 psig and a reaction time of about 1–8 hours.

Grane et al. U.S. Pat. No. 4,296,262 is directed to the manufacture of tertiary butyl alcohol from isobutane and oxygen and to the recovery of the tertiary butyl alcohol. Non-condensable gases such as oxygen, nitrogen, carbon dioxide, carbon monoxide, etc., are vented during the recovery process.

Kollar U.S. Pat. No. 3,351,635 discloses the reaction of tertiary butyl hydroperoxide with propylene to provide a reaction product comprising unreacted propylene, propylene oxide, and tertiary butyl alcohol. Related processes are disclosed, for example, in Marquis et al. U.S. Pat. No. 4,845,251 and Marquis et al. U.S. Pat. No. 4,891,437.

Sanderson et al. U.S. Pat. No. 4,900,850 discloses a reaction sequence wherein isobutane is reacted with oxygen to provide an oxidation reaction mixture comprising unreacted isobutane, tertiary butyl alcohol, tertiary butyl hydroperoxide and by-products. In accordance with one embodiment, tertiary butyl alcohol is recovered from the oxidation reaction mixture. In accordance with another embodiment, a solution of tertiary butyl hydroperoxide in tertiary butyl alcohol is recovered from the oxidation reaction mixture and reacted with propylene to provide an epoxidation reaction product comprising unreacted propylene, propylene oxide, an enhanced quantity of tertiary butyl alcohol, unreacted tertiary butyl hydroperoxide and by-products.

BACKGROUND INFORMATION

The off-gas fractions removed from isobutane oxidation reactors and propylene epoxidation reactors will contain not only inert gases such as nitrogen, oxygen, carbon monoxide, carbon dioxide, methanol, etc., but will also contain volatilized and/or entrained isobutane and propylene that will be lost to the system if the off-gas is immediately used as a fuel gas.

Tertiary butyl alcohol can be manufactured by the oxidation of isobutane to form an isobutane oxidation reaction product comprising tertiary butyl alcohol and tertiary butyl hydroperoxide. Tertiary butyl alcohol can be recovered from the isobutane oxidation reaction product by distillation or can be charged to a propylene epoxidation reaction zone together with tertiary butyl hydroperoxide to provide an epoxidation reaction product containing gaseous by-products, unreacted propylene, propylene oxide, unreacted tertiary butyl hydroperoxide, an enhanced amount of tertiary butyl alcohol and oxygen-containing by-products such as ditertiary butyl peroxide allyl tertiary butyl peroxide, isopropyl hydroperoxide, etc., and water.

The reaction products formed by the oxidation of isobutane with oxygen and by the epoxidation of tertiary butyl hydroperoxide with propylene will contain minor amounts of inert, non-condensable gases such as nitrogen, oxygen, carbon monoxide, carbon dioxide, methanol, etc. The inert gases are conventionally removed from the reaction vessels together with vaporized and/or entrained low boiling, normally liquid reaction product components and are cooled to partially recover normally liquid reaction product components from the inert gases. However, the cooled off-gas will still contain up to about 25 wt. % of light hydrocarbon components, principally isobutane from the isobutane oxidation reactor and up to about 75 wt. % of propylene from the propylene epoxidation reactor. When these off-gases are disposed of, the entrained isobutane and propylene are lost to the process.

SUMMARY OF THE PRESENT INVENTION

In accordance with the present invention, an isobutane oxidation product and/or a propylene epoxidation product is removed from a reactor, the reaction products contain inert gases and volatilized and/or entrained hydrocarbons such as isobutane or propylene. The gases are cooled to liquify hydrocarbons vapors and the remaining gaseous components, including volatilized and/or entrained hydrocarbons are passed through an absorption zone for the substantially complete removal of the remaining entrained hydrocarbons and the absorbed hydrocarbons are recovered from the resultant solution.

In accordance with one embodiment of the present invention, oxygen is reacted with isobutane in an oxidation reactor to provide a liquid reaction product and a gaseous oxidation product that will include vaporized and/or entrained normally liquid reaction product components. The gaseous oxidation products are removed from the oxidation reactor and cooled to condense normally liquid reaction product components contained therein and the remaining gases, including residual normally liquid reaction product components, principally isobutane, are charged to a tertiary butyl alcohol absorber where substantially all of the residual normally liquid reaction product components are absorbed to form an off-gas fraction and a solution of normally liquid reaction components in tertiary butyl alcohol.

In accordance with a modification of this embodiment of the present invention, oxygen is reacted with isobutane in an oxidation reactor to provide an isobutane oxidation product comprising gases, such as nitrogen, oxygen, carbon monoxide, carbon dioxide, methanol, etc., and normally liquid reaction components comprising isobutane, tertiary butyl alcohol, tertiary butyl hydroperoxide, etc. The gases, including vaporized and/or entrained normally liquid reaction product components are vented from the oxidation reactor and cooled to condense most of the normally liquid reaction product components, which are recycled to the oxidation reactor and the remaining gases, including residual normally liquid reaction product components, principally isobutane, are charged to a tertiary butyl alcohol absorber where substantially all of the residual normally liquid reaction product components are absorbed in the tertiary butyl alcohol. The remaining gases are vented from the absorber together with vaporized and/or entrained tertiary butyl alcohol and these gases are then charged to a water wash tower where the tertiary butyl alcohol is absorbed in the wash water to provide an aqueous solution of tertiary butyl alcohol and a fuel gas fraction. The aqueous solution of tertiary butyl alcohol is distilled to provide a lighter, lower boiling tertiary butyl alcohol fraction and a heavier higher boiling water fraction.

In accordance with another embodiment of the present invention, propylene, a solution of tertiary butyl hydroperoxide in tertiary butyl alcohol (formed, for example in the oxidation reactor) and molybdenum catalyst are charged to an epoxidation zone where the propylene is catalytically reacted with tertiary butyl hydroperoxide to form an epoxidation reaction product comprising low boiling reaction products, unreacted propylene, propylene oxide, an enhanced quantity of tertiary butyl alcohol, unreacted tertiary butyl hydroperoxide and oxygen-containing by-products. The epoxidation reaction product is charged to a propylene recovery distillation zone where it is separated into a gaseous fraction comprising vaporized and/or entrained normally liquid reaction product components a liquid propylene recycle fraction and a higher boiling distillation fraction comprising propylene oxide, tertiary butyl alcohol, unreacted tertiary butyl hydroperoxide and by products. The overhead gaseous fraction, including residual normally liquid reaction product components, principally propylene, is charged to a tertiary butyl alcohol absorber where substantially all of the residual normally liquid reaction product components are absorbed to form an off-gas fraction and a solution of normally liquid reaction components in tertiary butyl alcohol. The solution of normally liquid reaction components in tertiary butyl alcohol is charged to the propylene recovery distillation zone together with the epoxidation reaction product.

DETAILED DESCRIPTION OF THE PRESENT INVENTION

In general, in accordance with the present invention, a hydrocarbon oxidation reaction product is formed in an oxidation reactor by reacting isobutane with oxygen, the oxidation reaction product comprising gaseous reaction components and a liquid oxidation product. The liquid reaction product is fractionated in an isobutane recovery distillation zone. The gaseous reaction components, including non-condensable inert gases such as nitrogen, oxygen, carbon monoxide, carbon dioxide, methanol, etc., and normally liquid reaction components comprising unreacted feedstocks and oxygen-containing reaction products are cooled to remove entrained hydrocarbons. The gaseous components, including residual entrained hydrocarbons are passed through a tertiary butyl alcohol absorption zone where the residual entrained hydrocarbons are dissolved in tertiary butyl alcohol to form an off-gas fraction and a tertiary butyl alcohol solution of the residual entrained hydrocarbons. The off-gas fraction is discharged for further handling, (e.g., as a fuel gas) and the tertiary butyl alcohol solution is further processed.

The off-gas fraction will contain not only inert gases such as nitrogen, oxygen, carbon monoxide, carbon dioxide, methanol, etc., but will also contain volatilized and/or entrained tertiary butyl alcohol that will be lost to the system if the off-gas is immediately used as a fuel gas.

Accordingly, the off-gas fraction vented from the absorber is charged to a water wash tower where the tertiary butyl alcohol is absorbed in the wash water to provide an aqueous solution of tertiary butyl alcohol. The gases discharged from the water wash tower may suitably be used as fuel gas. The aqueous solution of tertiary butyl alcohol is distilled to provide a lighter tertiary butyl alcohol fraction and a lower boiling water fraction.

In accordance with another embodiment of the present invention, propylene, a solution of tertiary butyl hydroperoxide in tertiary butyl alcohol (recovered, for example in the isobutane recovery distillation zone) and a solution of a molybdenum catalyst are charged to an epoxidation reaction zone where the propylene catalytically reacts with tertiary butyl hydroperoxide to form an epoxidation reaction product comprising gaseous reaction products, unreacted propylene, propylene oxide, an enhanced quantity of tertiary butyl alcohol, unreacted tertiary butyl hydroperoxide and higher boiling by-products. The epoxidation reaction product is fractionated in a propylene recovery distillation zone to provide a gaseous fraction comprising vaporized and/or entrained normally liquid reaction product components a lower boiling liquid propylene recycle fraction and a higher boiling distillation fraction comprising propylene oxide, tertiary butyl alcohol, unreacted tertiary butyl hydroperoxide and by products. The overhead gaseous fraction, including residual normally liquid reaction product components, principally propylene, is charged to a tertiary butyl alcohol absorber where substantially all of the residual normally liquid reaction product components are absorbed to form an off-gas fraction and a solution of normally liquid reaction components in tertiary butyl alcohol. The solution of normally liquid reaction components in tertiary butyl alcohol is charged to the propylene recovery distillation zone together with the epoxidation reaction product.

In accordance with a preferred embodiment of the present invention, oxygen is reacted with isobutane in an oxidation reactor to provide an isobutane oxidation product comprising gases, isobutane, tertiary butyl alcohol, tertiary butyl hydroperoxide and oxygen-containing by-products. The gases, comprising inert gases and isobutane are processed as described above and a solution of tertiary butyl hydroperoxide in tertiary butyl alcohol is obtained from the isobutane oxidation product and charged to an epoxidation reactor together with propylene and a molybdenum catalyst. The propylene catalytically reacts with tertiary butyl hydroperoxide in the epoxidation reactor to form an epoxidation reaction product comprising gases and liquid products comprising propylene, propylene oxide, tertiary butyl alcohol, unreacted tertiary butyl hydroperoxide, oxygen-containing by-products such as ditertiary butyl peroxide allyl tertiary butyl peroxide, isopropyl hydroperoxide, etc., and water. The gases, comprising inert gases and propylene are processed as described above.

OXIDATION OF ISOBUTANE

The oxidation of isobutane with molecular oxygen is conducted in an oxidation reactor in liquid phase. The oxidation is preferably conducted at a moderate pressure because of the volatility of isobutane, such as a pressure of about 50 to 1000 psig. The oxidation reaction is suitably conducted at a temperature of about 40° to about 200° C., such as a temperature of about 80° to about 180° C. and more preferably, from about 90° to about 150° C. Reaction time and reaction conditions are correlated to provide for a desired conversion of the isobutane, such as a conversion of about 10 to about 75 wt. %, and more preferably from about 20 to about 50 wt. %. The composition of a representative oxidation reaction product is given in Table 1.

TABLE 1

COMPOSITION OF TYPICAL OXIDATION REACTION PRODUCT

| Component | General Range, Wt. % | Preferred Range, Wt. % |
|---|---|---|
| Isobutane | 25–90 | 50–80 |
| t-butyl hydroperoxide | 70–0 | 25–55 |
| t-butyl alcohol | 0–70 | 25–55 |
| Others* | 0.5–10 | 0.5–3 |

*Includes di-tertiary butyl peroxide, acetone, methanol, acetic acid, formic acid, isobutyric acid and other oxygenated impurities including allyl tertiary butyl peroxide, isopropyl hydroperoxide, etc., and water.

Volatile materials that are present in the oxidation reactor will comprise inert non-condensable gases such as nitrogen, oxygen, carbon monoxide, carbon dioxide, methanol, etc., and vaporized and/or entrained normally liquid reaction product components, principally isobutane.

The liquid oxidation product, after being withdrawn from the oxidation reactor is normally charged to a distillation zone where it is separated into a lighter, lower boiling isobutane recycle fraction and a heavier higher boiling debutanized fraction comprising the remaining components of the liquid oxidation reaction product.

SYNTHESIS OF PROPYLENE OXIDE AND TERTIARY BUTYL ALCOHOL

The heavier higher boiling debutanized liquid oxidation reaction product fraction is charged to an epoxidation reactor together with propylene and a solution of a soluble molybdenum catalyst.

The debutanized liquid oxidation reaction product that is charged to the epoxidation reactor is preferably charged as a tertiary butyl alcohol solution of tertiary butyl hydroperoxide comprising at least about 30 wt. % of tertiary butyl alcohol and about 40 to 70 wt. % of tertiary butyl hydroperoxide.

Suitable molybdenum catalysts include soluble molybdenum compounds such as molybdenum octoate, molybdenum naphthenate, molybdenum acetyl acetonate, molybdenum/alcohol complexes, molybdenum/glycol complexes, etc., such as a complex prepared in the manner described in U.S. Pat. No. 4,626,596 by reacting an ammonium-containing molybdenum compound such as ammonium heptamolybdate tetrahydrate or ammonium dimolybdate hydrate with an alkylene glycol such as ethylene glycol or propylene glycol. The catalyst concentration is operably within the range of 50 to 1,000 ppm, based on the total reactant charge and is preferably in the range of about 200 to 600 ppm.

The epoxidation reaction may be conducted at a temperature in the range of about 50° to about 180° C., preferably between 90° and 140° C. and more preferably between about 100° to about 130° C.

The reaction time can be varied within comparatively wide limits, but will generally run from about 2.5 to 4 hours, and more preferably from 0.5 to 1.5 hours. Preferably the reaction is conducted in a series of reactors, such as a series of continuous stirred reactors followed by a series of plug flow reactors.

The epoxidation reaction product will normally comprise gaseous by-products, propylene, propylene oxide, tertiary butyl alcohol, tertiary butyl hydroperoxide, impurities and higher boiling oxygen-containing by-products and is normally withdrawn from the reactor and charged to a product recovery zone where it is separated into suitable recycle, product and by-product fractions (see, for example, Meyer et al. U.S. Pat. No. 5,101,052, Meyer et al. U.S. Pat. No. 5,106,458, and/or Smith et al. U.S. Pat. No. 5,127,997).

Volatile materials that are present in the epoxidation reactor will comprise inert, non-condensable gases such as nitrogen, oxygen, carbon monoxide, carbon dioxide, methanol, etc., and vaporized and/or entrained normally liquid reaction product components, principally propylene.

BRIEF DESCRIPTION OF THE DRAWING

The drawing is a schematic flow sheet with conventional parts omitted showing the general reaction and recovery sequence of the present invention for recovering low boiling hydrocarbons such as propylene and isobutane.

DESCRIPTION OF THE PREFERRED EMBODIMENT

Turning now to the drawing, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

An oxidation reactor 10 is schematically shown in the drawing. Oxygen is charged to the reactor 10 by a line 12 and isobutane is charged by a line 14.

Autocatalytic oxidation reaction conditions are established in the oxidation reactor 10 correlated to provide an initial reaction product comprising unreacted isobutane, peroxide reaction products including tertiary butyl hydroperoxide, ditertiary butyl peroxide, etc., tertiary butyl alcohol, oxygenated impurities including methanol and acetone, water, nitrogen, oxygen, carbon monoxide, carbon dioxide, etc. Suitably, the autocatalytic reaction conditions used in the oxidation reactor 10 will include a temperature of about 100° to about 150° C., a pressure of about 50 to about 1000 psig, and a reaction time of about 1 to about 8 hours. Vaporized reaction product components, including methanol, isobutane, and acetone, nitrogen, oxygen, carbon monoxide, carbon dioxide, etc., and normally liquid reaction product components entrained therein are withdrawn from the reactor 10 by a line 30 for further processing. A liquid reaction product comprising the remainder of the reaction product (e.g., isobutane, tertiary butyl hydroperoxide, ditertiary butyl peroxide, tertiary butyl alcohol, and high boiling oxygenated impurities and by-products is continuously withdrawn from the oxidation reactor 10 by way of a discharge line 16 leading to a first distillation zone (e.g., column) 20 wherein the initial reaction product is fractionated under conditions selected to provide for a first overhead fuel gas fraction 21, a first lower boiling distillation fraction 22 consisting essentially of isobutane and a first higher boiling distillation fraction comprising the remainder of the initial liquid reaction product, which is discharged by way of a line 24. All or a portion of the isobutane in the line 22 may be recycled to the isobutane charge line 14 for the oxidation reactor 10.

The vaporized reaction product components are charged by the line 30 to a heat-exchanger 32 where they are cooled by an amount sufficient to condense most of the isobutane and entrained normally liquid reaction product components (e.g., a temperature of about 100° C.) and the resulting mixture is charged by a line 34 to a drum 36 where the condensate is collected for recycle by a condensate recycle line 38 leading to oxidation reactor 10.

The remaining vapors comprising isobutane and inert reaction product components such as methanol, acetone, nitrogen, oxygen, carbon monoxide, carbon dioxide, etc., are discharged from the drum 36 by a line 40 leading to the overhead line 21 from the first distillation column 20.

The first overhead fuel gas fraction 21 is fed to a charge point adjacent the bottom of a tertiary butyl alcohol wash column 50. Tertiary butyl alcohol is charged to the tertiary butyl alcohol wash column 50 adjacent the top thereof by a line 52 for counter-current contact with the charged vapors in the tertiary butyl alcohol wash column 50 under extraction conditions of time, temperature and contact time sufficient to absorb substantially all of the isobutane in the tertiary butyl alcohol.

A solution of isobutane in tertiary butyl alcohol is discharged from the tertiary butyl alcohol wash column 50 by a line 54 leading back to first distillation column 20.

The overhead from tertiary butyl alcohol wash column 50 comprising the inert gases and entrained and/or vaporized tertiary butyl alcohol is discharged by overhead line 56 leading to a point adjacent the bottom of a water wash tower 60. Water is charged to the water wash column 60 adjacent the top thereof by a line 62 for counter-current contact with the charged vapors in the water wash column 60 under extraction conditions of time, temperature and contact time sufficient to absorb substantially all of the tertiary butyl alcohol in water.

The un-absorbed inert gases (principally nitrogen, oxygen, carbon monoxide and carbon dioxide) are discharged from the top of water wash column 60 by a vent line 64 for discharge from the system.

An aqueous solution of tertiary butyl alcohol is discharged from water wash column 60 by a discharge line 66 leading to offsite facilities (not shown) for the recovery of tertiary butyl alcohol.

In accordance with a preferred embodiment of the present invention, the higher boiling fraction 24 from first distillation column 20, which comprises a tertiary butyl alcohol solution of tertiary butyl hydroperoxide and minor amounts of by-products such as ditertiary butyl peroxide, and other high boiling oxygenated impurities is charged to an epoxidation reactor 100 together with propylene charged to reactor 100 by a propylene supply line 102. A solution of a soluble molybdenum catalyst in a suitable solvent (e.g., an alkylene glycol such as ethylene glycol, propylene glycol, diethylene glycol, dipropylene glycol, etc.) is charged to the reactor 100 by a catalyst supply line 104. Epoxidation reaction conditions are established in the epoxidation reactor 100, whereby the propylene will react with the tertiary butyl hydroperoxide to provide an epoxidation reaction mixture comprising propylene, propylene oxide, additional tertiary butyl alcohol, tertiary butyl hydroperoxide and impurities and reaction by-products. The epoxidation reaction product is discharged from the epoxidation reactor 100 by a line 108 leading to a second distillation zone 110 where it is separated into a second overhead fraction 112, and a second higher boiling fraction 114 comprising tertiary butyl alcohol.

The second overhead fraction 112 is charged to a third distillation column 200 where it is separated into a third overhead fraction 202, a third lower boiling propylene fraction 204 that is suitably recycled to the propylene charge line 102 and a third higher boiling fraction 206 comprising propylene oxide and reaction by-products.

The third overhead fraction 202 is charged to a second tertiary butyl alcohol wash column 150 at a charge point adjacent the bottom thereof. Tertiary butyl alcohol is charged to the second tertiary butyl alcohol wash column 150 adjacent the top thereof by a line 152 for counter-current contact with the charged vapors in the second tertiary butyl alcohol wash column 150 under extraction conditions of time, temperature and contact time sufficient to absorb substantially all of the propylene in the tertiary butyl alcohol.

A solution of propylene in tertiary butyl alcohol is discharged from the second tertiary butyl alcohol wash column 150 by a line 154 for recycle to the second distillation zone 110. The overhead from second tertiary butyl alcohol wash column 150 comprising the inert gases, a small amount of propylene and entrained and/or vaporized tertiary butyl alcohol is discharged by overhead line 156.

What is claimed is:

1. A method which comprises the steps of:
    a) reacting oxygen with isobutane in an oxidation reactor to provide a gaseous reaction product comprising inert gases and vaporized and/or entrained isobutane and a liquid reaction product comprising isobutane, tertiary butyl alcohol, tertiary butyl hydroperoxide and oxygen-containing by-products,
    b) charging the liquid reaction product to a distillation zone and separating it therein into a lower boiling isobutane fraction and a higher boiling fraction comprising tertiary butyl alcohol and tertiary butyl hydroperoxide and oxygen-containing by-products,
    c) cooling the gaseous reaction product by an amount sufficient to condense isobutane contained therein,
    d) returning the isobutane condensate to the oxidation reactor, and
    e) charging the remaining gases, including entrained and/or vaporized isobutane, to a tertiary butyl alcohol absorber and absorbing substantially all of the residual isobutane in tertiary butyl alcohol to form a solution of isobutane in tertiary butyl alcohol, and an off-gas fraction.

2. A method as in claim 1 wherein the off-gas fraction from the tertiary butyl alcohol absorber is charged to a water wash tower to absorb entrained tertiary butyl alcohol in the wash water to provide an aqueous solution of tertiary butyl alcohol, and distilling the aqueous solution of tertiary butyl alcohol to provide a lower boiling tertiary butyl alcohol fraction and a higher boiling water fraction.

3. A method which comprises the steps of:
    a) reacting oxygen with isobutane in an oxidation reactor to provide a gaseous reaction product comprising inert gases and vaporized and/or entrained isobutane and a liquid reaction product comprising isobutane, tertiary butyl alcohol, tertiary butyl hydroperoxide and oxygen-containing by-products,
    b) charging the liquid reaction product to a first distillation zone and separating it therein into a first lower boiling isobutane fraction and a first higher boiling fraction comprising tertiary butyl alcohol, tertiary butyl hydroperoxide and oxygen-containing by-products,
    c) cooling the gaseous reaction product by an amount sufficient to condense isobutane contained therein,
    d) returning the isobutane condensate to the oxidation reactor,
    e) charging the remaining gases, including isobutane, to a tertiary butyl alcohol absorber and absorbing substantially all of the residual isobutane in tertiary butyl alcohol to form a solution of isobutane in tertiary butyl alcohol, and an off-gas fraction, f) charging the off-gas fraction from the tertiary butyl alcohol absorber to a water wash tower to absorb entrained tertiary butyl alcohol in the wash water to provide an aqueous solution of tertiary butyl alcohol, g) charging the first higher boiling fraction comprising a solution of tertiary butyl hydroperoxide in tertiary butyl alcohol, to an epoxidation reactor together with propylene and a molybdenum epoxidation catalyst and epoxidizing the propylene therein with tertiary butyl hydroperoxide to form a liquid epoxidation reaction product comprising propylene, propylene oxide, additional tertiary butyl alcohol, tertiary butyl hydroperoxide, impurities and reaction by-products, h) removing the reaction product comprising propylene, propylene oxide, additional tertiary butyl alcohol, tertiary butyl hydroperoxide and impurities, reaction by-products and molybdenum catalyst from the reactor, i) charging the liquid reaction product to a third distillation zone and fractionating it therein to provide an overhead fraction containing propylene, a third lower boiling propylene recycle fraction and a fourth higher boiling fraction comprising the remaining liquid reaction product components, and j) charging the overhead fraction to a tertiary butyl alcohol absorber to absorb substantially all of the propylene in tertiary butyl alcohol to form a solution of propylene in tertiary butyl alcohol and an off-gas fraction.

* * * * *